US008324356B2

(12) United States Patent
Picotti et al.

(10) Patent No.: US 8,324,356 B2
(45) Date of Patent: Dec. 4, 2012

(54) POLYSACCHARIDE DERIVATIVES OF LIPOIC ACID, AND THEIR PREPARATION AND USE AS SKIN COSMETICS AND MEDICAL DEVICES

(75) Inventors: Fabrizio Picotti, Buttrio (IT); Marco Bosco, Gradisca D'Isonzo (IT); Luca Stucchi, Risano (IT); Matteo Fabbian, Trieste (IT)

(73) Assignee: Sigea S.R.L., Trieste (IT)

( * ) Notice: Subject to any disclaimer, the term of this patent is extended or adjusted under 35 U.S.C. 154(b) by 217 days.

(21) Appl. No.: 12/808,885

(22) PCT Filed: Dec. 11, 2008

(86) PCT No.: PCT/EP2008/010534
§ 371 (c)(1),
(2), (4) Date: Jun. 17, 2010

(87) PCT Pub. No.: WO2009/080220
PCT Pub. Date: Jul. 2, 2009

(65) Prior Publication Data
US 2010/0255097 A1    Oct. 7, 2010

(30) Foreign Application Priority Data
Dec. 21, 2007 (IT) .............................. MI2007A2416

(51) Int. Cl.
*C08B 37/08* (2006.01)
*C07H 19/00* (2006.01)
*C07H 5/04* (2006.01)
*C07H 15/06* (2006.01)

(52) U.S. Cl. .......... 536/20; 536/21; 536/55.1; 536/55.2; 536/55.3

(58) Field of Classification Search ........................ None
See application file for complete search history.

(56) References Cited

U.S. PATENT DOCUMENTS

| | | | |
|---|---|---|---|
| 2,589,226 A | | 3/1952 | Carson |
| 6,288,106 B1 * | | 9/2001 | Pearson et al. ................ 514/440 |
| 2004/0171581 A1 * | | 9/2004 | Rastrelli et al. ................ 514/54 |
| 2004/0265268 A1 | | 12/2004 | Jain |
| 2007/0207116 A1 | | 9/2007 | Brown |

FOREIGN PATENT DOCUMENTS

| | | |
|---|---|---|
| WO | 00/01733 | 1/2000 |
| WO | 03/008457 | 1/2003 |
| WO | 2006/128618 | 12/2006 |
| WO | 2007/105854 | 9/2007 |

OTHER PUBLICATIONS

Kofuji et al., "Stabilization of aplha-lipoic acid by complex formation with chitosan" Food Chemistry, vol. 109, No. 1, Dec. 14, 2007, pp. 167-171.
Liebert et al., "Synthesis and Characterization of Cellulose alpha-lipoates: A Novel Material for Adsorption onto Gold" Polymer Bulletin, vol. 57, No. 6, Aug. 7, 2006, pp. 857-863.
Hornig et al., "Synthesis and Characterization of Sulfur Containing Dextran and beta-cyclodextrin derivatives" Polymer Bulletin, vol. 59, No. 1, Mar. 9, 2007, pp. 65-71.

* cited by examiner

*Primary Examiner* — Layla Bland
(74) *Attorney, Agent, or Firm* — Lucas & Mercanti, LLP

(57) ABSTRACT

Disclosed are polysaccharides containing residues of glucosamine or galactosamine in the repetitive unit, characterized by the presence of esters on the hydroxyls or amides on the amine functions, with lipoic acid or with mixtures of lipoic acid and formic acid.

26 Claims, 3 Drawing Sheets

Figure 1:
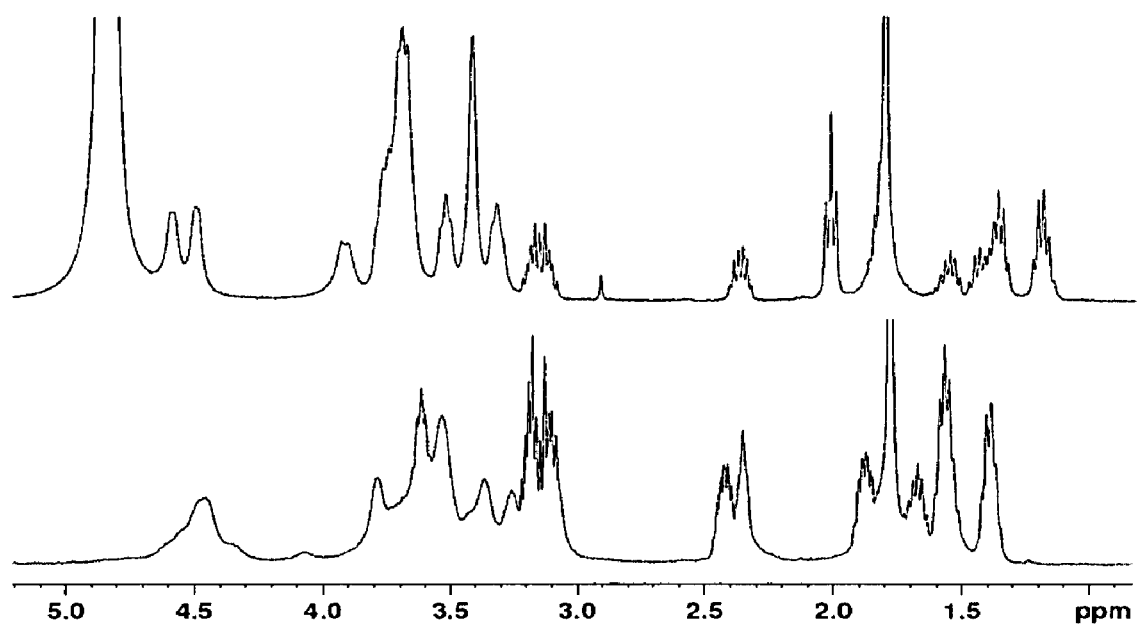

POLYSACCHARIDE DERIVATIVES OF LIPOIC ACID, AND THEIR PREPARATION AND USE AS SKIN COSMETICS AND MEDICAL DEVICES

This application is a U.S. national stage of PCT/EP2008/010534 filed on Dec. 11, 2008, which claims priority to and the benefit of Italian Application No. MI2007A002416 filed on Dec. 21, 2007, the contents of which are incorporated herein by reference.

SUMMARY OF THE INVENTION

The present invention discloses novel polysaccharide derivatives containing glucosamine or galactosamine residues in the repetitive unit, characterised by the presence of esters on the hydroxyls or amides on the amine functions, with lipoic acid or with mixtures of lipoic acid and formic acid, their preparation by an original synthesis method wherein the formate ester, if any, originates from formamide, and their purification and use as skin protection substances.

STATE OF THE ART

Lipoic acid (or thioctic acid) is a natural molecule, isolated in mammal livers, which acts as an essential cofactor for many enzymatic reactions, including the conversion of pyruvate to Acetyl-CoA in the Krebs cycle. Lipoic acid is a potent antioxidant which prevents the symptoms of vitamin C and vitamin E deficiency, and also a powerful scavenger of reactive species, namely free radicals such as hydroperoxides, superoxides, peroxynitrites, etc.

Esters of some polysaccharides are known, such as cellulose with lipoic acid; lipoic acid esters with synthetic polymers (PEG); lipoic acid esters or amides with small molecules, and formulations based on physical mixtures of lipoic acid or derivatives thereof with hyaluronic acid (HA) (and derivatives thereof) or with chondroitin sulphate (CS).

Materials based on microcrystalline cellulose derivatised with lipoic acid by esterification under homogenous conditions in dimethylacetamide (DMAc)/LiCl with carbonyldiimidazole (CDI) at the temperature of 60° C. have been described (Polymer Bulletin, 57, 2006, pp 857-863). The products obtained tend to chelate gold atoms, and are therefore suitable to coat gold leaf to produce supports for biomineralisation, crystal growth and immobilisation of enzymes. Cellulose esters with lipoic acid are reported which have a maximum degree of substitution (DS) of 1.45, and are insoluble in common solvents from DS 0.50.

Dextran and beta-cyclodextrin derivatised with lipoic acid by esterification under homogenous conditions in DMSO with CDI at the temperature of 80° C. (one-pot reaction) have been described (Polymer Bulletin, 59, 2007, pp 65-71). Dextran esters with lipoic acid which have a maximum DS of 0.44, and beta-cyclodextrin esters with lipoic acid which have a maximum DS of 1.99, both insoluble in common solvents, have been reported. Said materials are designed to produce surface coatings for systems able to interact with biological or organic molecules.

Microcrystalline cellulose derivatised with lipoic acid by esterification under homogenous conditions in DMAc/LiCl with dicyclohexyl-carbodiimide (DCC) and dimethylaminopyridine (DMAP) at the temperature of 40° C. has been described (Macromolecular Bioscience, 7, 2007, DOI: 10.1002/mabi. 200700110). The products obtained demonstrate antioxidant activity of potential use in the manufacture of blood-compatible membranes for use in the haemodialysis process (chemical and biomedical industry), and have a maximum DS of 0.58. Said polymer products show an increase in metabolic stability and a decline in the breakdown rate of the antioxidant molecule bonded to them. Said polymers are required to have a molecular weight sufficiently high to ensure that they do not cross the blood-brain barrier and damage the cell membranes.

WO 2007/105854 discloses the synthesis of water-soluble esters of lipoic acid with polyethylene glycol (PEG with various molecular weights) for use in external topical applications as an antioxidant, bleaching agent and anti-aging product; it describes a process of derivatisation of lipoic acid by EDCI (1-ethyl-3-(3'-dimethyaminopropyl)carboimide) and DMAP.

WO 02/076935 describes novel derivatives of lipoic acid obtained by means of an amide bond of lipoic acid to aminoacids. Said products show biological activity.

U.S. Pat. No. 6,365,623 discloses a topical formulation for the treatment of acne based on lipoic acid and ester and amide derivatives thereof. HA is mentioned as a further additive in the formulation.

WO 2006/128618 discloses novel formulations based on lipoic acid and HA or derivatives thereof for use in the pharmaceutical and cosmetic fields, due to their effect of regenerating damaged skin, preventing skin aging and repairing chronic ulcers. Said formulations can be administered topically or systemically (orally, by injection, etc.).

WO 2005/041999 describes novel formulations for diet supplements designed to improve the joint functions, reduce inflammation and repair cartilage. The various possible components mentioned include chondroitin sulphate and lipoic acid.

However, no examples of lipoic acid covalently bonded via an ester or amide bond to glycosaminoglycans or chitosan are reported in the literature.

DESCRIPTION OF THE INVENTION

The present invention discloses novel polysaccharide derivatives containing residues of glucosamine or galactosamine in the repetitive unit partly esterified or amidated with lipoic acid, or with lipoic acid and formic acid simultaneously.

The degree of substitution (DS) of lipoic esters on the hydroxyls of each polysaccharide monomer ranges between 0.01 and 0.5*N in the case of esters and between 0.01 and 1 for amides, where N is the number of free alcohol groups present in the repetitive unit, while the degree of esterification of formic acid on the polymer hydroxyl groups, when it is present, is between 0.01 and 0.2 (ie. between 1% and 20%). The polysaccharides derivatised according to the invention are glycosaminoglycans (hyaluronic acid, chondroitin sulphate, dermatan sulphate, heparan sulphate and cheratan sulphate) and chitosan; in this latter case, the bond between polymer and lipoic acid is an amide bond, and involves the amine group at the 2-position of the glucosamine residue.

The carboxyl function of the polysaccharide derivatives may be salified with alkaline metals, in particular sodium.

The molecular weight of the polysaccharide falls into the interval between $10^3$ and $10^7$ daltons, and between $10^4$ and $10^6$ daltons in the case of the hyaluronic acid derivative. The latter will preferably have a degree of esterification of lipoic acid at the hydroxyl groups of the polymer ranging between 0.01 and 0.8, while the degree of esterification of formic acid at the hydroxyl groups of the polymer is between 0 and 0.20, and the degree of crosslinking is between 0.001 and 0.1, as regards the ester groups between two different hyaluronic acid chains.

The degree of esterification or amidation can be modulated according to the characteristics of the starting polysaccharide and the reaction conditions used, such as the stoichiometric ratios between polysaccharide substrate and activated lipoic acid, the type and quantity of catalytic base used, and the reaction temperature. For example, in the case of hyaluronic acid lipoic derivatives, by changing the synthesis conditions it is possible to obtain soluble straight-chain polymers or crosslinked hydrogels containing, in addition to lipoic esters, esters between the hydroxyl groups of one chain and the carboxyl groups of the glucuronic acid unit belonging to a different chain. This latter bond constitutes the crosslinking bridge. The hydrogels acquire significant viscoelastic properties, which have been studied from the rheological standpoint and are described below.

The straight-chain (non-crosslinked) derivatives according to the invention can be used in topical compositions with a moisturising, elasticising, toning, anti-aging or anti-acne action or as adjuvants for the treatment of skin lesions such as inflammations, ulcers, wounds, dermatitis, and skin hyperthermia caused by radiation. The polysaccharide concentration may be between 0.05% and 5% by weight of the composition. Examples of suitable formulations include creams, ointments, gels, hydrophilic liquids, aqueous or water-alcohol lotions, oil/water or water/oil emulsions.

The crosslinked derivatives, in hydrogel form, can be introduced into sterile syringes and used as medical devices for intra-articular use as viscosupplementation agents and skin fillers in cosmetic surgery. The medical devices according to the invention will contain a hydrogel of hyaluronic acid lipoate swollen in sterile saline solution, at a polymer concentration of between 0.5% and 3% weight/volume.

A medical device containing a hyaluronic acid derivatised according to the invention, with a molecular weight ranging between $10^4$ and $10^6$ daltons, can also be advantageously used as eyedrops for the treatment of forms of conjunctivitis and keratitis with different etiologies.

The invention also relates to the process for the preparation thereof, which comprises:
  a. Dissolution of the selected polysaccharide in the form of an alkaline metal (generally sodium) salt, or in chlorinated form in the case of chitosan, in an organic solvent, in particular formamide (FA);
  b. Activation of lipoic acid through carbonyldiimidazole solubilised in an organic solvent such as dimethylacetamide (DMA), FA, DMF, DMSO, etc., in particular DMA, thereby obtaining lipoyl-imidazolide;
  c. Addition to the polymer solution of a basic catalyst, preferably dimethylaminopyridine (DMAP) or triethylamine, and of the solution containing lipoyl-imidazolide, in the chosen quantities; in the synthesis of autocrosslinked hyaluronic acid lipoate the basic catalyst is avoided, and an excess of carbonyldiimidazole is used.
  d. Reaction at a controlled temperature (usually room temperature) for defined times, followed by dilution of the reaction mixture with a solution buffered to physiological pH;
  e. Purification of the end products by precipitation, dialysis or tangential filtration;
  f. Recovery of the product by filtration, freeze-drying or spray-drying.

The base is an aromatic or aliphatic organic base comprising one atom of trisubstituted nitrogen, preferably dimethylaminopyridine, 4-pyrrolidine-pyridine or triethylamine. The solubilisation temperature of the polysaccharide in formamide is typically between 60° C. and 120° C., and preferably 95° C.

In the case of crosslinked hyaluronic acid, the process comprises the following steps:
  a) dissolving hyaluronic acid salified with sodium or other alkaline metals in formamide, by heating;
  b) adding to the resulting solution, lipoic acid pre-activated with carbonyldiimidazole, at room temperature;
  c) reacting the reaction mixture at room temperature for between 4 and 24 hours;
  d) diluting the reaction mixture with a buffered aqueous solution and neutralising it to pH 6-7.5;
  e) purifying the dilute reaction mixture by dialysis;
  f) freezing the purified aqueous polysaccharide solution and recovering the product by freeze-drying.

Formate ester, when present, originates in the process according to the invention by hydrolysis of formamide under the experimental conditions used.

The following examples describe in detail the synthesis of some polysaccharide derivatives of lipoic acid according to this invention.

EXAMPLES

The $^1$H NMR tests are carried out in $D_2O$ or DMSO-d6 with a Bruker Avance 400 spectrometer equipped with a 5 mm multinuclear probe with a z gradient, at 300° K. The tests include Diffusion Ordered Spectroscopy (DOSY); these latter experiments demonstrate the existence of a covalent bond between the polymer and lipoic acid. Quantitation of the esterified lipoic acid residues (degree of substitution, DS) is performed after exhaustive hydrolysis with NaOD directly in the NMR tube. The $^1$H spectrum of the hydrolysate allows the signals attributable to lipoic acid and those attributable to the polysaccharide to be integrated; their ratio provides the DS. Similarly, the DS is evaluated in formate esters, when present.

Example 1

Synthesis of Hyaluronic Acid Lipoic Ester 1.50 grams of HA sodium salt is solubilised in 30 ml of formamide (5.0% w/v) at 95° C. for 2 hours; the temperature is then reduced to 25° C., and 911 mg of DMAP is added to the solution. 770 mg of lipoic acid is solubilised separately in 2.0 ml of DMA, and reacted with 604 mg of CDI for 30 min. at 25° C. The resulting solution containing the lipoylimidazolide is dropped into the solution of HA, DMAP and formamide, and the reaction proceeds under mechanical stirring for 20 hours at 25° C. 300 ml of water containing a phosphate buffer ($KH_2PO_4/K_2HPO_4$), 0.25M at pH 6, is then added, and purification by dialysis is performed. The aqueous solution is then frozen and freeze-dried. 1.48 g of lyophilisate is recovered.

10 mg of sample is solubilised in 0.7 ml of $D_2O$ and transferred to an NMR tube.

FIG. 1 shows the $^1$H NMR spectra of hyaluronic acid lipoic ester before (bottom) and after (top) hydrolysis of the esters by adding NaOD.

The bottom spectrum is obtained by applying a DOSY sequence which only retains the signals attributable to chemical groups covalently bonded to the polymer.

A DS value of 0.50 is obtained from integration of the methylene signals associated with lipoic acid (FIG. 1); the DS in formate amounts to 0.02.

Example 2

Synthesis of Hyaluronic Acid Lipoic Ester without the Use of a Catalyst 125 mg of HA sodium salt is solubilised in 5 ml of formamide (2.5% w/v) at 95° C. for 2 hours; the temperature is then reduced to 25° C. 192 mg of lipoic acid is solubilised separately in 1 ml of DMA, and reacted with 151 mg of CDI for 30 min. at 25° C. The resulting solution containing the lipoylimidazolide is dropped into the HA and formamide solution, and the reaction proceeds under stirring for 20 hours at 25° C. The sample is recovered by precipitation in acetone. After two washes in acetone and drying under vacuum, 112 mg of sample is recovered.

10 mg of sample is solubilised in 0.7 ml of DMSO-d6 acidified with TFA while hot, and transferred to the NMR tube. A DS value of 0.25 is obtained from integration of the methylene signals associated with lipoic acid.

Example 3

Synthesis of Hyaluronic Acid Lipoic Ester Purified by Ultrafiltration 250 mg of HA sodium salt is solubilised in 5 ml of formamide (5.0% w/v) at 95° C. for 2 hours; the temperature is then reduced to 25° C., and 152 mg of DMAP is added to the solution. 128 mg of lipoic acid is solubilised separately in 0.6 ml of DMA, and reacted with 101 mg of CDI for 30 min. at 25° C. The resulting solution containing the lipoylimidazolide is dropped into the HA, DMAP and formamide solution, and the reaction proceeds under stirring for 20 hours at 25° C. The sample is recovered by ultrafiltration. 225 mg of sample is frozen and recovered by freeze-drying.

10 mg of sample is solubilised in 0.7 ml of $D_2O$ and transferred to an NMR tube. A DS value of 0.47 is obtained from integration of the methylene signals associated with lipoic acid; the DS in the formate residues amounts to 0.04.

Example 4

Synthesis of Straight-Chain Hyaluronic Acid Lipoic Ester with a High Degree of Substitution 250 mg of HA sodium salt is solubilised in 5 ml of formamide (5.0% w/v) at 95° C. for 2 hours; the temperature is then reduced to 25° C., and 228 mg of DMAP is added to the solution. 385 mg of lipoic acid is solubilised separately in 1.5 ml of DMA, and reacted with 302 mg of CDI for 30 min. at 25° C. The resulting solution containing the lipoylimidazolide is dropped into the HA, DMAP and formamide solution, and the reaction proceeds under stirring for 20 hours at 25° C. The sample is recovered by precipitation in acetone. After two washes in acetone and drying under vacuum, 220 mg of sample is recovered.

10 mg of sample is solubilised in 0.7 ml of DMSO-d6 acidified while hot with TFA, and transferred to an NMR tube. A DS value of 1.8 is obtained from integration of the methylene signals associated with lipoic acid; the DS in the formate residues amounts to 0.07.

Example 5

Synthesis of Crosslinked Hyaluronic Acid Lipoic Ester 500 mg of HA sodium salt is solubilised in 10 ml of formamide (5.0% w/v) at 95° C. for 2 hours; the temperature is then reduced to 25° C. 180 mg of lipoic acid is solubilised separately in 1 ml of DMA, and reacted with 202 mg of CDI for 30 min. at 25° C. The resulting solution containing the lipoylimidazolide is dropped into the HA solution in formamide, and the reaction proceeds under mechanical stirring for 20 hours at 25° C. 30 ml of water is then added, the pH is adjusted to 6.5 with solid $KH_2PO_4$, and purification by dialysis is performed. The aqueous solution is then frozen and freeze-dried. 490 mg of crosslinked lyophilisate is recovered, as demonstrated by the rheological studies illustrated in FIGS. 2 and 3.

10 mg of sample is solubilised in 0.7 ml of $D_2O$, pH 11, and transferred to an NMR tube. A DS value of 0.10 is obtained from integration of the methylene signals associated with lipoic acid; the DS in the formate residues amounts to 0.02.

Example 6

Synthesis of Chondroitin Sulphate Lipoic Ester 1.0 grams of CS sodium salt is solubilised in 5 ml of formamide (20% w/v) at 80° C. for 20 minutes; the temperature is then reduced to 25° C., and 488 mg of DMAP is added to the solution. 412 mg of lipoic acid is solubilised separately in 1.0 ml of DMA, and reacted with 324 mg of CDI for 30 min. at 25° C. The resulting solution containing the lipoylimidazolide is dropped into the CS, DMAP and formamide solution, and the reaction proceeds under mechanical stirring for 20 hours at 25° C. 20 ml of water is then added, the pH is adjusted to 7 with solid 0.5M HCl, and purification by ultrafiltration is performed. The aqueous solution is then frozen and freeze-dried. 850 mg of lyophilisate is recovered.

10 mg of sample is solubilised in 0.7 ml of $D_2O$ and transferred to an NMR tube. A DS value of 0.70 is obtained from integration of the methylene signals associated with lipoic acid; the DS in the formate residues amounts to 0.02.

Example 7

Synthesis of Lipoic Chitosan Amide 200 mg of freeze-dried chitosan hydrochloride (obtained by solubilising chitosan flakes in water acidified with hydrochloric acid at pH 3, and then freeze-drying the solution) was solubilised in 4 ml of formamide (5.0% w/v) at 95° C. for 10 min. 104 mg of lipoic acid was solubilised separately in 0.5 ml of DMA, and reacted with 82 mg of CDI for 30 min. at 25° C. The resulting solution containing the lipoylimidazolide is dropped into the chitosan and formamide solution, and the reaction proceeds under mechanical stirring for 20 hours at 25° C. 20 ml of water is then added, the pH is adjusted to 7 with 0.5M HCl, and purification is performed by dialysis. The aqueous solution is then frozen and freeze-dried. 171 mg of lyophilisate is recovered.

10 mg of sample is solubilised in 0.7 ml of $D_2O$ acidified with trifluoroacetic acid and transferred to an NMR tube. A DS value of 0.23 is obtained from integration of the methylene signals associated with lipoic acid; the DS in the formate residues amounts to 0.03.

Example 8

Preparation of an O/W Elasticising Cream

A non-limiting example of the invention, which illustrates the preparation of a cream formulation containing one of the lipoic acid esters according to the invention, is set out below.

The O/W cream formulation contains the compound described in example 1 as functional agent, at the concentration of 0.1%, suitably mixed with common excipients used in skin cosmetics, such as emulsifiers, thickeners, oils, moisturisers, gelling agents, preservatives, etc.

Briefly, the process is as follows:

Approximately 600 ml of demineralised water (corresponding to approx. 60% by weight of the total formulation) is loaded into a turboemulsifier, and the pre-melted fatty phase is added under stirring at approx. 70° C. The mixture is emulsified, and cooled slowly to the temperature of 35-40° C. The thermolabile and volatile constituents are added at this temperature, followed by the HA sodium salt lipoic ester described in example 1, dissolved in a suitable quantity of water. The mixture is left under slow stirring until the temperature of 25-30° C. is reached, and the finished product is then discharged into a suitable container.

The result is a cream with the following composition (% W/W):

| | |
|---|---|
| Sodium HA lipoic ester (Example 1) | 0.1 |
| Oils (palmitic/caprylic glycerides-triglycerides) | 12 |
| Non-ionic emulsifiers | 6 |
| Cetyl alcohol | 2 |
| Dimethicone | 4 |
| MgAl silicate | 2 |
| Glycerin | 3 |
| Xylitol | 2 |
| Parabens | 0.7 |
| $H_2O$ | q.s. to 100 |

Example 9

Preparation of a Medical Device in the Form of a Syringe Containing 1.5 ml of a Hydrogel Containing 2% w/w of Crosslinked HA Lipoate Obtained as Described in Example 5

30 mg of autocrosslinked esterified polymer in lyophilisate form, obtained as described in example 5, is weighed in a sterile 2.0 ml syringe; the syringe is filled with 1.47 g of an aqueous solution of 0.9% NaCl (w/V). All the experimental procedures are conducted under a laminar-flow hood using endotoxin-free materials; the above-mentioned saline solution is also prepared with water for injectable use. The polymer is left to swell for 24 hours at room temperature. The syringe is then steam-sterilised in accordance with a standard cycle at 121° C. for 16 minutes in the autoclave.

Rheological Study of Hyaluronic Acid Esterified with Lipoic Acid and Autocrosslinked A comparative rheological study was conducted on two samples of hyaluronic acid lipoic ester obtained under different experimental conditions: the first, described in example 1, was solubilised in water to provide a viscous solution, while the second, described in example 5, provided a microgel dispersion. A commercial hyaluronic acid solution with a molecular weight of Mw=300 kDa, employed for the two syntheses, was used as reference. All three systems contained the same weight concentration of polymer (2%), and were prepared with the same saline solution (0.3% w/w NaCl, acetate buffer 20 mM at pH=5.5).

The rheology measurements were conducted with a Rheostress Haake RS150 controlled-stress rotational rheometer able to exert both sinusoidal and linear stresses on the sample; the sample deformation rate was measured at the same time. The rheometer was equipped with flat smooth or knurled plates. The measurements were thermostated at 25° C.

Figure 2:
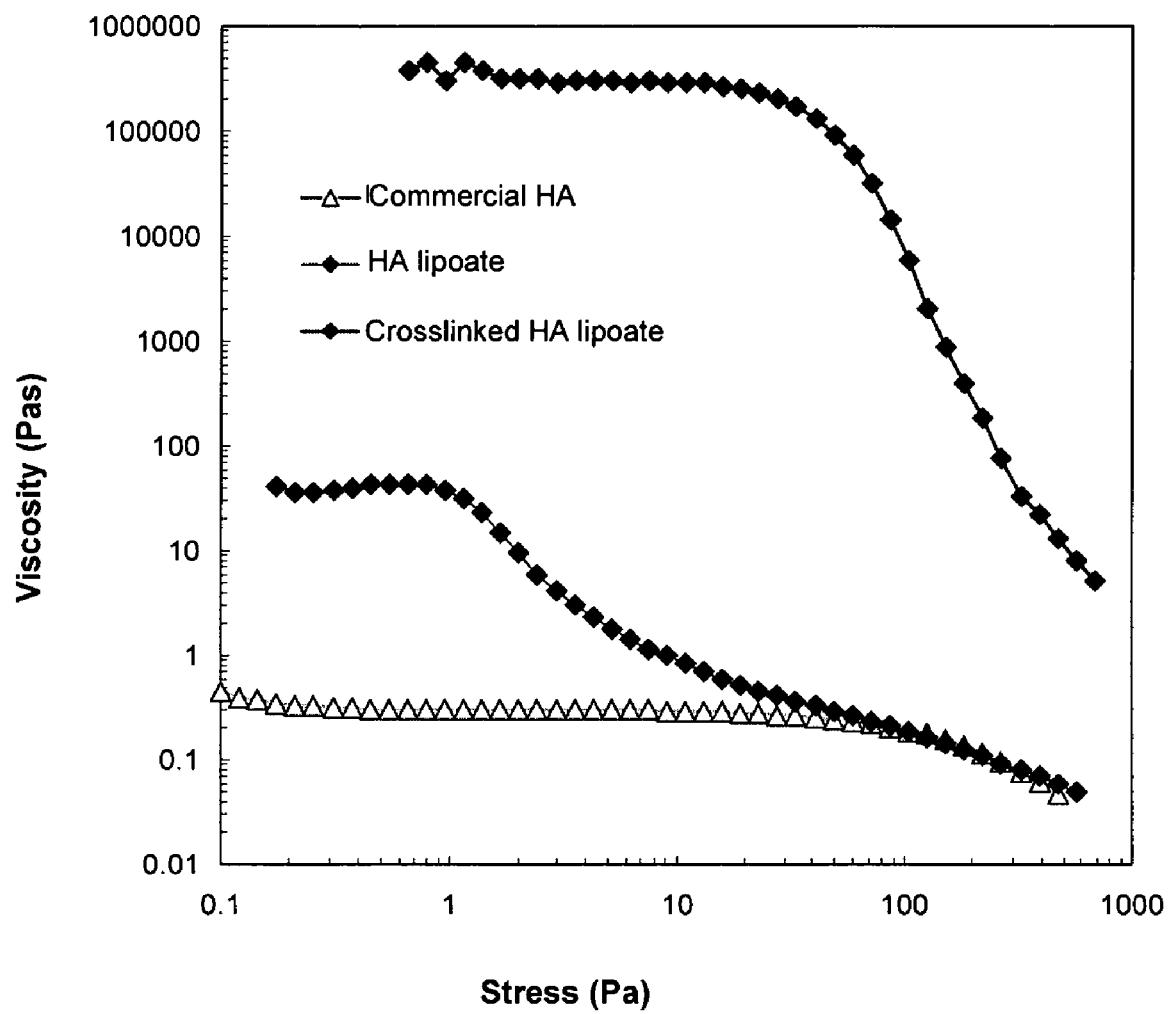

Flow curves that measure viscosity on variation of the stress applied were recorded on the three samples compared (FIG. 2).

The viscosity of the three systems with low stress differs by several orders of magnitude, and the flow curves change dramatically from a profile typical of a viscous liquid (commercial HA) to that of an elastic solid (HA lipoate and crosslinked HA).

Figure 3:
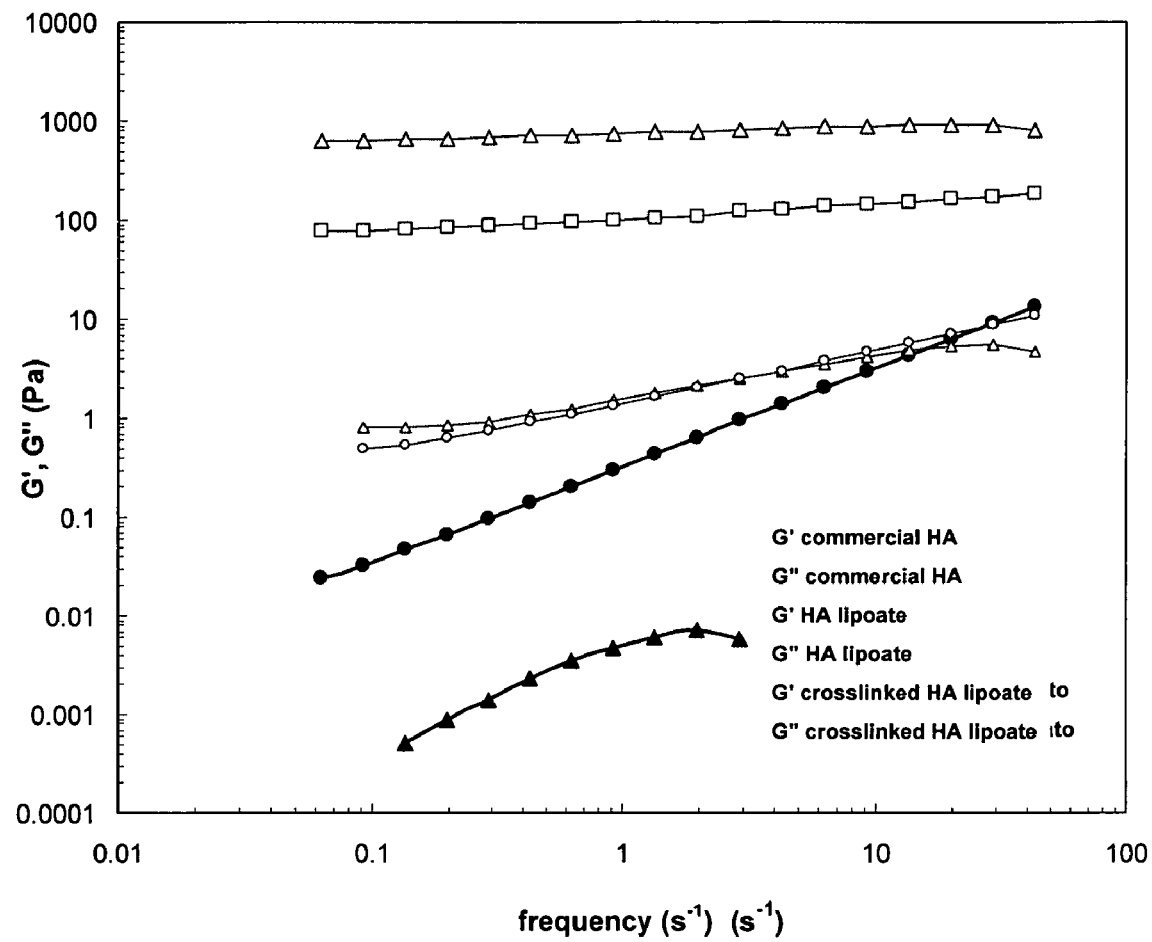

FIG. 3 shows the mechanical spectra of the three different systems. In the typical behaviour of a solution, the viscous modulus (G") is greater than the elastic modulus (G') at low frequencies, while as the oscillation frequency increases, the two modules tend to cross. This behaviour is observed for the straight-chain ester lipoate solution (Example 1). In the typical profile of a gel, the modulus of elasticity prevails over the viscous modulus throughout the oscillation frequency range, and is practically constant. This trend is observed in the microgel dispersion prepared according to Example 5.

The invention claimed is:

1. Chitosan or glycosaminoglycans selected from the group consisting of hyaluronic acid, chondroitin sulphate, dermatan sulphate, heparan sulphate and keratan sulphate comprising repetitive units which are partly esterified on hydroxyls or amidated on amine functions with lipoic acid or with mixtures of lipoic acid and formic acid.

2. Glycosaminoglycans as claimed in claim 1, wherein carboxyl functions and sulphate groups of the glycosaminoglycans are present in acid form or salified with alkaline metals.

3. Chitosan or Glycosaminoglycans as claimed in claim 1, wherein the molecular weight of the chitosan or of the glycosaminoglycan is between $10^3$ and $10^7$ daltons.

4. Glycosaminoglycans as claimed in claim 1, wherein the glycosaminoglycan is hyaluronic acid with a molecular weight included between $10^4$ and $10^6$ daltons.

5. Glycosaminoglycans as claimed in claim 1, wherein the degree of esterification of said lipoic acid on the hydroxyl groups of each of the repetitive units is between 0.01 and 0.5*N, where N is the number of free alcohol groups present in the repetitive unit, while the degree of esterification of formic acid on the hydroxyls groups of each of the repetitive units is between 0 and 0.20.

6. Chitosan as claimed in claim 1 wherein the degree of amidation of lipoic acid on the chitosan amine group is between 0.01 and 1, while the degree of esterification of said formic acid on the chitosan hydroxyl groups is between 0 and 0.20.

7. Glycosaminoglycans as claimed in claim 5, wherein the glycosaminoglycan is hyaluronic acid, and the degree of esterification of lipoic acid on the hydroxyls of the glycosaminoglycan is between 0.01 and 0.8, while the degree of esterification of formic acid on the hydroxyls of the glycosaminoglycan is between 0 and 0.20.

8. Glycosaminoglycans as claimed in claim 1, wherein the glycosaminoglycan is hyaluronic acid, and the degree of esterification of lipoic acid on the hydroxyls of the glycosaminoglycan is between 0.01 and 0.8, the degree of esterification of formic acid on the hydroxyls of the glycosaminoglycan is between 0 and 0.20, and the hydroxyls groups of the hyaluronic acid of one chain of the glycosaminoglycan and the carboxyl groups of the hyaluronic acid of a different chain of the glycosaminoglycan are crosslinked in a degree between 0.001 and 0.1.

9. Process for the preparation of the chitosan and glycosaminoglycans claimed in claim 1, said process comprising:
   a) dissolving in formamide chitosan or a glycosaminoglycan in salified form or a glycosaminoglycan salified with sodium or other alkaline metals, by heating to obtain a solution;
   b) adding to the resulting solution lipoic acid pre-activated by carbonyldiimidazole in the presence of an organic base, at room temperature to obtain a reaction mixture;
   c) reacting the reaction mixture at room temperature for between 1 and 24 hours;
   d) diluting the reaction mixture of step c) with a buffered aqueous solution and neutralizing it to pH 6-7.5;
   e) purifying the dilute reaction mixture by precipitation with a suitable solvent, dialysis or tangential filtration; and
   f) recovering the product by filtration or spray-drying, or freezing the purified aqueous chitosan or glycosaminoglycan solution and recovering the product by freeze-drying.

10. Process as claimed in claim 9, wherein the base is an aromatic or aliphatic organic base comprising one atom of trisubstituted nitrogen.

11. Process for the preparation of cross-linked hyaluronic acid chains as claimed in claim 8, which comprises the following steps:
   a) dissolving in formamide hyaluronic acid salified with sodium or other alkaline metals by heating to obtain a solution;
   b) adding to the resulting solution lipoic acid pre-activated with an excess of carbonyldiimidazole, at room temperature to obtain a reaction mixture;
   c) reacting the reaction mixture at room temperature for between 4 and 24 hours;
   d) diluting the reaction mixture of step c) with a buffered aqueous solution and neutralizing it to pH 6-7.5;
   e) purifying the dilute reaction mixture by dialysis; and
   f) freezing the purified aqueous hyaluronic acid solution and recovering the product by freeze-drying.

12. Process as claimed in claim 9, wherein the temperature of solubilisation of the chitosan or glycosaminoglycan in formamide is between 60° C. and 120° C.

13. Topical compositions comprising the chitosan or the glycosaminoglycans derivatives claimed in claim 1, and inert, dermatologically acceptable excipients.

14. Topical compositions as claimed in claim 13, containing the chitosan or the glycosaminoglycans in percentages of between 0.05% and 5% by weight of the composition.

15. Topical compositions as claimed in claim 13, in the form of creams, ointments, gels, hydrophilic liquids, aqueous or water-alcohol lotions, oil/water or water/oil emulsions.

16. Chitosan or glycosaminoglycans as claimed in claim 1 as topical moisturising, elasticising, toning, antioxidant, anti-radical, anti-aging and anti-acne agents.

17. Chitosan or glycosaminoglycans as claimed in claim 1 for the treatment, as adjuvants, of skin lesions.

18. Chitosan or glycosaminoglycans as claimed in claim 1 for the treatment of skin lesions caused by inflammation, chronic ulcers, wounds, atopic or contact dermatitis, and radiation-induced skin hyperthermia.

19. Medical device in the form of a syringe containing a hydrogel of cross-linked hyaluronic acid derivative prepared as claimed in claim 11, swollen in sterile saline solution at a polymer concentration of between 0.3% and 3% weight/volume.

20. Medical device as claimed in claim 19, as viscosupplementation agent for intra-articular application.

21. Medical device as claimed in claim 19, as skin filler for cosmetic surgery applications.

22. Medical device containing a hyaluronic acid derivative as claimed in claim 4 as eyedrops for treating forms of conjunctivitis and keratitis.

23. Glycosaminoglycans as claimed in claim 2, wherein the alkaline metal is sodium.

24. Process as claimed in claim 9, wherein the temperature of solubilisation of the chitosan or the glycosaminoglycan in formamide is 95° C.

25. Process as claimed in claim 10, wherein said base comprises dimethylaminopyridine, 4-pyrrolidine-pyridine or triethylamine.

26. Process as claimed in claim 11, wherein the temperature of solubilisation of the hyaluronic acid in formamide is 95° C.

* * * * *